United States Patent
Newman et al.

[11] Patent Number: 6,114,548
[45] Date of Patent: Sep. 5, 2000

[54] DIELS-ALDER REACTION OF ALDEHYDES WITH SIMPLE DIENES

[75] Inventors: Christopher Paul Newman, Canterbury; Varinder Kumar Aggarwal, Broomhill; Graham Patrick Vennall, Bexhill, all of United Kingdom

[73] Assignee: Quest International B.V., Netherlands

[21] Appl. No.: 09/008,768

[22] Filed: Jan. 19, 1998

[30] Foreign Application Priority Data

Jan. 21, 1997 [EP] European Pat. Off. ............. 97300377

[51] Int. Cl.$^7$ .................................................. C07D 309/00
[52] U.S. Cl. ........................................................... 549/356
[58] Field of Search ............................................. 549/356

[56] References Cited

U.S. PATENT DOCUMENTS 4,709,085  11/1987  Nugent et al. .
4,847,392   7/1989  Gassman et al. .

FOREIGN PATENT DOCUMENTS 13822  10/1971  Australia .
0 325 000   7/1989  European Pat. Off. .
08266625    7/1997  Japan .

OTHER PUBLICATIONS

Chemical Abstracts, vol. 1, No. 7, Aug. 13, 1979, Columbus, Ohio, US; Abstract No. 56685y, XP002063880.
Chemical Abstracts, vol. 126, No. 26, Jun. 30, 1997, Columbus, Ohio, US; Abstract No. 343460t, XP002063881.
Chemical Abstracts, vol. 127, No. 9, Sep. 1, 1997, Columbus, Ohio, US; Abstract No. 121610y, XP002063882.
J. Inanaga et al.; New J. Chem., vol. 19, 1995, pp. 707–712, XP002049944.
S. Oi et al., Tetrahedron Letters, vol. 37, No. 35, 1996, Oxford GB, pp. 6351–6354, XP002063879.
H. Griengl et al. Monatshofte for Chemie, vol. 107, 1976; Wein At, pp. 675–684, XP002063877.
M.F. Ansell et al.; Journal of the Chemical Society, Chemical Communications, 1972, Letchworth GB, pp. 73990740. XP002063877.
Catalyzed Adhesions of Nucleophilic Alkenes to C = pp. 534–561.
Tetrahedron Letters, vol. 34, No. 15; pp. 2409–2413.
Synlett, Mar. 1996; A New Scandium Complex as an Extremely Active Acylation Catalyst; pp. 265–266.
Tetrahedron Letters, vol. 37, No. 35; pp. 6351–6354, 1996. Catalyzed Additions of Nucleophilic Alkenes to C=X; 2.1 The Prins and Carbonyl Ene Reactions; Barry B. Snider, p. 527–533.
Synthesis, Jun. 1994, Asymmetric Hetero Diels–Alder Reactions, p. 535–551.
New J. Chem. 1995, 19, p. 707–712; Achiral and Chiral Lanthanide Salts of Superacids as Novel Lewis Acid Catalysts in Organic Synthesis.
Synlett, Sep. 1994, p. 689–701.
T. Imamols/Academic Press, p. 102–111.
New J. Chem. 1995, 19, 713–722 p. 973–977.

*Primary Examiner*—Johann Richter
*Assistant Examiner*—Joseph Murray

[57] ABSTRACT

The invention concerns Diels-Alder reactions between non-activated aldehydes RCHO in which R is a C1–C10 aliphatic group or phenyl group, which is unsubstituted or substituted with one or more C1–C5 alkyl groups or one other functional group, with simple aliphatic dienes $R_1CH=CR_2-CR_3=CHR_4$ in which $R_1$–$R_4$ are H or C1–C5 alkyl groups using as a catalyst a perfluorinated organic sulphonic acid or a Brönsted acid derivative thereof. The reaction leads to dihydropyrans of the structure below in which R1–R4 have the meaning indicated above.

The preferred perfluorinated organic sulfonic acids are perfluorooctanesulphonic acid, triflic acid, Nafion or a Brönsted acid derivative of triflic acid.

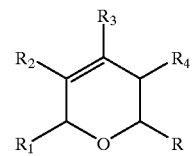

The preferred aldehydes are those wherein R is a C2–C6 aliphatic group or a phenyl group which is unsubstituted or mono-substituted with C1–C3 alkyl or with 4-Cl, 4-nitro or 3-methoxy. The preferred dienes are those wherein the groups $R_1$–$R_4$ are H or methyl.

11 Claims, No Drawings

DIELS-ALDER REACTION OF ALDEHYDES WITH SIMPLE DIENES

The invention relates to catalysed Diels-Alder reactions between non-activated aldehydes and simple dienes leading to dihydropyrans.

The hetero Diels-Alder (D-A) reaction between aldehydes and dienes has been limited mainly to the reaction of either highly electron rich dienes (Danishefsky's and similar dienes) with a broad range of aldehydes, or of highly activated aldehydes (e.g. chloral and glyoxylates) with a broad range of dienes, see e.g. H Waldmann, Synthesis 1994, 535. Recently the reaction between simple dienes and unactivated aldehydes has been achieved using a cationic $Pd^{2+}$ catalyst, see: S. Oi et al, Tet. Letters., 37 (1996), 6351. Furthermore, the Lewis acid catalysed D-A reaction of non-activated aldehydes and simple dienes has been described in U.S. Pat. No. 5,162,551 in which a mixture of $AlCl_3$ or $SnCl_4$ with nitroalkanes (particularly 2-nitropropane) is used. The reported yields are good, but the catalyst system is potentially explosive and difficult to handle. J. Inanaga. New J. Chem. 1995 19, 707 reported the use of lanthanide (III) salts of superacids such as trifluoromethanesulfonic acid (triflic acid, TfOH) and perfluorooctanesulfonic acid (PfOH) as catalysts in D-A reactions. He reports that with 30 mole % of $Yb(OPf)_3$ and $Sc(OPf)_3$ high yields of 2-phenyl-4,5-dimethyl-2,3-dihydropyran were obtained from benzaldehyde and 2,3-dimethyl-butadiene. With $Sc(OTf)_3$ only moderate yields were obtained.

Furthermore, various reactions between simple aliphatic dienes and non-activated aldehydes catalysed by strong Brönsted acids and leading to 5,6-dihydropyrans have been reported as outlined below. This reaction has also been categorized as a Prins-type reaction.

i AU 13822/70: formaldehyde+1,3-butadiene with sulphuric acid;

ii M. F. Ansell and A. A. Charalambides, J.C.S. Chem. Comm., 1972, 739: benzaldehyde+2,3-dimethyl-butadiene with p-toluene-sulphonic acid at 80° C.;

iii H. Griengl and K. P. Geppert, Monatsh. Chem. 107 (1976), 675: 1,3-butadiene, isoprene or 2,3-dimethyl-1,3-butadiene+benzaldehyde with concentrated sulphuric acid.

In i very low yields were reported, in ii the reaction had to be carried out at 80° C. and in iii a tenfold excess of aldehyde was used and moreover, the reaction with isoprene and with 1,3-butadiene produced a complicated reaction mixture.

The D-A reaction between non-activated aromatic aldehydes and simple aliphatic dienes is particularly useful for preparing dihydropyrans. Examples are the fragrance materials 6-phenyl-4-methyl-5,6-dihydropyran, also known as Rosyrane, 6-phenyl-2,4-dimethyl-dihydropyran and 6-butyl-2,4-dihydropyran. Rosyrane is itself a starting material for the preparation of the fragrance material Mefrosol, also known as Phenoxanol, through reductive ringopening in acidic media (see U.S. Pat. No. 5,162,551).

Although the use of the above mentioned lanthanide salts would appear to give good prospects for such D-A reactions, lanthanide salts are expensive, a high molar ratio of catalyst (30 mole %) appears to be required and lanthanide salts of perfluorooctanesulfonic acid are high molecular weight materials. The latter means that high amounts of solid material need to be handled which adds considerably to the production costs.

It has now been found that non-activated aldehydes RCHO, in which R is a C1–C10 aliphatic group or phenyl group which is unsubstituted or substituted with one or more C1–C5 alkyl groups or one other functional group, may be reacted in a D-A reaction with simple aliphatic dienes $R_1CH=CR_2$—$CR_3=CHR_4$, in which $R_1$–$R_4$ are H or C1–C5 alkyl groups, using as a catalyst a perfluorinated organic sulphonic acid or a Brönsted acid derivative thereof.

Thus, the invention provides a process for the preparation of 5,6-dihydropyrans of the general formula: in which the groups R and $R_1$–$R_4$ have the meaning given above, comprising reacting the corresponding aldehyde with the corresponding diene under the influence of a perfluorinated organic sulphonic acid or a Brönsted acid derivative thereof.

Preferred are perfluorooctanesulphonic acid, triflic acid, polymeric perfluoroalkanesulfonic acids such as those known as Nafion*, as well as Brönsted acid derivatives of triflic acid, particularly trifluoromethanesulfonimide (triflimide). The acids can be pure, but need not necessarily be water-free.

\* Trademark of Dupont de Nemours of Wilmington Del.

Preferably the groups $R_1$–$R_4$ are H or methyl, more preferably at most two of $R_1$–$R_4$ are methyl and the others are hydrogen. Particularly preferred dienes are isoprene, 2,3-dimethyl-butadiene, 1,3-dimethyl-butadiene and 1,3-pentadiene.

R is preferably a C2–C6 aliphatic group or a phenyl group which is unsubstituted or mono-substituted with C1–C3 alkyl or with 4-Cl, 4-nitro or 3-methoxy. Particularly preferred phenyl groups are: phenyl and 4-methylphenyl.

The aldehyde/diene ratio does not have much influence on the course of the reaction. Ratios between 10:1 and 1:20 are suitable and between 5:1 and 1:10 are preferred. In practice an about equimolar ratio or slight excess of diene works very well.

The amount of catalyst is preferably chosen between 0.01 and 50 mol % based on the reactant being present in lowest molar amount, more preferably between 0.1 and 20%, most preferably between 0.2 and 15%.

The reaction is conveniently carried out in an organic solvent. This does not necessarily have to be completely water-free, as would be necessary with many Lewis acid catalysts. Preferred are low polarity or non-polar solvents; particularly preferred are hydrocarbons such as hexane, cyclohexane, toluene and petroleum spirit.

The reaction is conveniently carried out above −10° C. and below +80° C., more preferably between 0 and 60° C., most preferably between 10 and 40° C. Ambient reaction temperatures and pressures are most convenient from a practical point of view, although higher pressures may sometimes be useful, e.g. with volatile dienes. Since the reaction is not very exothermic no expensive measures have to be taken to keep the reaction temperature within the desired limits.

The reaction proceeds regioselectively, leading predominantly to one positional isomer if an unsymmetric diene is used. Thus, the reaction between benzaldehyde and isoprene leads to 4-methyl-6-phenyl-5,6-dihydropyran. Some double bond isomerisation may take place leading to the presence of the 4-methylene- and/or the 2,3-dihydro-isomers in the reaction product The reaction mixtures can be worked up in the usual way and the reaction product isolated and purified by conventional means such as distillation, chromatographic techniques and the like. Non-aqueous work-up is particularly convenient as it reduces the amount of waste water.

EXAMPLE 1

Preparation of 4-methyl-6-phenyl-5,6-dihydropyran

To a rapidly stirred solution of 70% aqueous triflic acid (2.10 g, 0.01 mol) and benzaldehyde (106.1 g, 1.0 mol) in 100 ml toluene was added isoprene (150 cm$^3$, 1.5 mol) over 4 hrs. at 25° C. The mixture was stirred at room temperature for a further 11 hours after which the reaction mixture was quenched by the addition of Polyrad* (2 g) and solid sodium carbonate (5 g). The crude mixture was distilled under reduced pressure to give pure rosyrane (56% yield) as a colorless oil.

* Trademark of Hercules for polyethoxylated abietyl amine.

EXAMPLES 2–6

Under the same conditions the following aldehydes and dienes were reacted, leading to the indicated yields of the corresponding dihydropyran (GC detected yield given):

| Aldehyde | Diene | Yield (%) |
| --- | --- | --- |
| benzaldehyde | isoprene | 72 |
| 4-methyl-benzaldehyde | isoprene | 65 |
| 4-Cl-benzaldehyde | isoprene | 68 |
| benzaldehyde | 2,3-dimethylbutadiene | 85 |
| benzaldehyde | 1,3-dimethylbutadiene | not det. |

EXAMPLE 7

Bis-trifluoromethanesulphonimide (70, 5 mg, 0.25 mmol) was stirred in hexane (4 ml) at room temperature. Benzaldehyde (510 μl, 5.0 mmol) and isoprene (750 μl, 7.5 mmol) were added and the mixture stirred at room temperature overnight. Water (5 ml) was added and the aqueous layer was extracted with hexane (3×3 ml). The combined organic layers were filtered through celite and analysed by glc. A yield of 42% of 4-methyl-6-phenyl-5,6-dihydropyran was observed.

What is claimed is:

1. A process for the preparation of 5,6-dihydropyrans of the general formula:

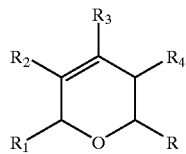

in which R is a C1–C10 aliphatic group or phenyl group which is unsubstituted or substituted with one or more C1–C5 alkyl groups or one other functional group and in which $R_1$–$R_4$ are H or C1–C5 alkyl groups, comprising reacting the corresponding aldehyde RCHO with the corresponding diene $R_1CH{=}CR_2{-}CR_3{=}CHR_4$ in the presence of a catalyst comprising a perfluorinated organic sulphonic acid or a Brönsted acid derivative thereof.

2. The process according to claim 1 wherein the perfluorinated organic sulfonic acid is perfluoro-octanesulphonic acid, triflic acid, polymeric perfluoroalkanesulfonic acid or a Brönsted acid derivative of triflic acid.

3. The process according to claim 2 wherein the Brönsted acid derivative of triflic acid is trifluoromethanesulfonimide or bis-trifluoromethane-sulfonimide.

4. The process according to claim 1 wherein R is a C2–C6 aliphatic group or a phenyl group which is unsubstituted or mono-substituted with C1–C3 alkyl or with 4-Cl, 4-nitro or 3-methoxy.

5. The process according to claim 1 wherein the groups $R_1$–$R_4$ are H or methyl.

6. The process according to claim 1 wherein the aldehyde/diene ratio is between 10:1 and 1:20.

7. The process according to claim 1 wherein the amount of catalyst is between 0.01 and 50 mol % based on the reactant being present in the lowest molar amount.

8. The process according to claim 5 wherein at most two of the groups $R_1$–$R_4$ are methyl and the others are hydrogen.

9. The process according to claim 6 wherein the aldehyde/diene ratio is between 5:1 and 1:10.

10. The process according to claim 7 wherein the amount of catalyst is between 0.1 and 20 mol % based on the reactant being present in the lowest molar amount.

11. The process according to claim 10 wherein the amount of catalyst is between 0.2 and 15 mol % based on the reactant being present in the lowest molar amount.

* * * * *